(12) United States Patent
Jorge et al.

(10) Patent No.: US 9,078,584 B2
(45) Date of Patent: Jul. 14, 2015

(54) ELECTROENCEPHALOGRAM ELECTRODE UNIT FOR SMALL ANIMALS AND MEASUREMENT SYSTEM USING THE SAME

(75) Inventors: Riera Jorge, Miyanagi (JP); Akira Sumiyoshi, Miyanagi (JP); Ryuta Kawashima, Miyanagi (JP)

(73) Assignee: TOHOKU UNIVERSITY, Sendai-shi (JP)

( * ) Notice: Subject to any disclaimer, the term of this patent is extended or adjusted under 35 U.S.C. 154(b) by 200 days.

(21) Appl. No.: 13/641,834

(22) PCT Filed: Apr. 21, 2011

(86) PCT No.: PCT/JP2011/059876
§ 371 (c)(1),
(2), (4) Date: Feb. 5, 2013

(87) PCT Pub. No.: WO2011/132756
PCT Pub. Date: Oct. 27, 2011

(65) Prior Publication Data
US 2013/0131461 A1 May 23, 2013

(30) Foreign Application Priority Data
Apr. 21, 2010 (JP) .................................. 2010-098320

(51) Int. Cl.
*A61B 5/0478* (2006.01)
*A61B 5/0408* (2006.01)
*A61B 5/055* (2006.01)

(52) U.S. Cl.
CPC ............. *A61B 5/0478* (2013.01); *A61B 5/0408* (2013.01); *A61B 5/04085* (2013.01); *A61B 5/055* (2013.01)

(58) Field of Classification Search
CPC .................................................... A61B 5/0478

USPC .................................................... 600/383, 544
See application file for complete search history.

(56) References Cited

U.S. PATENT DOCUMENTS 5,348,006 A * 9/1994 Tucker .......................... 600/383
6,602,220 B1 8/2003 Ludvig et al.
(Continued)

FOREIGN PATENT DOCUMENTS

DE 202008007953 U1 11/2008
JP 1-167206 U 11/1989
(Continued)

OTHER PUBLICATIONS

S.M. Mirsattari et al, "EEG Monitoring during Functional MRI in Animal Models", Epilepsia, vol. 48, pp. 37-46, 2007.
(Continued)

*Primary Examiner* — Lee S Cohen
(74) *Attorney, Agent, or Firm* — Westerman, Hattori, Daniels & Adrian, LLP

(57) ABSTRACT

The electroencephalogram electrode unit for small animals includes a base that covers the scalp or brain surface of a small animal and has a plurality of through holes and a plurality of electrodes. Each of the plurality of electrodes is inserted into each of the plurality of through holes, and each of the plurality of electrodes is equipped with an insulating tube, an electrode section disposed within the tube, an extraction conducting wire that is connected to the electrode section and extracts the EEG signal to outside, and a paste that is filled within the tube. The tube is installed in the through hole in a manner of standing upright from the scalp or brain surface, and the electrode section is formed in the form of a wire and is disposed, in a manner of standing upright from the scalp or brain surface, within the paste filled within the tube.

8 Claims, 18 Drawing Sheets

(56) References Cited

U.S. PATENT DOCUMENTS

| | | | |
|---|---|---|---|
| 7,930,013 B2* | 4/2011 | Ponton | 600/383 |
| 2007/0083097 A1 | 4/2007 | Fujiwara et al. | |
| 2008/0275359 A1* | 11/2008 | Mintz et al. | 600/544 |

FOREIGN PATENT DOCUMENTS

| | | |
|---|---|---|
| JP | 05-115451 A | 5/1993 |
| JP | 2002-272691 A | 9/2002 |
| JP | 2006-149562 A | 6/2006 |
| JP | 2006-318450 A | 11/2006 |
| JP | 2008-018017 A | 1/2008 |
| WO | 00/27279 A1 | 5/2000 |
| WO | 2007/059069 A2 | 5/2007 |
| WO | 2009/104644 A1 | 8/2009 |
| WO | 2009/134763 A1 | 11/2009 |

OTHER PUBLICATIONS

P. Megevand et al, "A mouse model for studying large-scale neuronal networks using EEG mapping techniques", NeuroImage, vol. 42, pp. 591-602, Feb. 2008.

S. Ogawa et al, "Brain magnetic resonance imaging with contrast dependent on blood oxygenation", Proc. Natl. Acad. Sci. USA, vol. 87, No. 24, pp. 9868-9872, Dec. 1990.

P. Tallgren et al, "Evaluation of commercially available electrodes and gels for recording of slow EEG potentials", Clinical Neurophysiology, vol. 116, pp. 799-806, 2005.

International Search Report for PCT/JP2011/059876, mailing date of Aug. 9, 2011.

Extended European Search Report dated Jul. 17, 2014, issued in corresponding application No. 11772088.8 (6 pages).

* cited by examiner (A)

(B)

(A)

(B)

(A)

(B)

(A)

(B)

(A)

(B)

ELECTROENCEPHALOGRAM ELECTRODE UNIT FOR SMALL ANIMALS AND MEASUREMENT SYSTEM USING THE SAME

TECHNICAL FIELD

The present invention relates to an electroencephalogram electrode unit for small animals and a measurement system using the same. More specifically, the present invention relates to an electroencephalogram electrode unit for small animals and a measurement system using the same capable of performing electroencephalogram measurement, f-MRI and other measurements simultaneously.

BACKGROUND ART

Magnetic resonance imaging (MRI) is a method of imaging information within a living body using nuclear magnetic resonance phenomenon. Furthermore, the f-MRI has recently been developed. The f-MRI stands for functional magnetic resonance imaging, and is one of the methods of imaging brain functions using MRI. The changes in the neuronal activities in local areas of the brain result in the changes in the nuclear magnetic resonance imaging signals, which is the principle of the f-MRI.

Furthermore, the electroencephalogram (EEG) for living bodies has conventionally been performed. A number of simultaneous electroencephalogram (EEG) and f-MRI measurements have recently been conducted in research institutes worldwide for living humans. For example, Patent Reference 1 discloses a helmet for electroencephalogram measurement for humans. Patent Reference 2 discloses an electrode for electroencephalogram measurement for humans.

Meanwhile, with small animals such as rats, which have smaller brain volume than humans, large electrodes disclosed in Patent References 1 and 2 cannot be used. With EEG for small animals, it is difficult to fasten small electrodes to limited brain space, and it is also difficult to maintain low impedance generated between the scalp and the electrodes. Consequently, few reports have been made on simultaneous EEG and f-MRI measurement techniques for small animals due to such technical difficulties.

With the conventional simultaneous EEG and f-MRI measurement techniques for small animals, the metal or carbon electrode was only placed and fastened to the brain surface of small animal, which is why there are only a few successful examples of simultaneous EEG and f-MRI measurements for small animal (such as rat and mouse) (See Non-patent References 1 and 2). Furthermore, since EEG measurement in such EEG-f-MRI measurement uses a single electrode (See Non-patent Reference 1), electroencephalogram can be detected only partially and it is therefore not effective when the target of study is the entire brain.

Patent References 3 and 4 disclose systems using a plurality of measurement lines or electrodes for EEG.

PRIOR TECHNICAL REFERENCE

Patent Reference

Patent Reference 1: JP 1993-115451A
Patent Reference 2: JP 2008-018017A
Patent Reference 3: WO 2007/59069
Patent Reference 4: U.S. Pat. No. 6,602,220

Non-Patent Reference

Non-patent Reference 1: S. M. Mirsattari, J. R. Ives, L. S. Leung, and R. S. Menon, "EEG Monitoring during Functional MRI in Animal Models", Epilepsia, Vol. 48, pp. 37-46, 2007

Non-patent Reference 2: P. Megevand, C. Quairiaux, A. M. Lascano, J. Z. Kiss, and C. M. Michel, "A mouse model for studying large-scale neuronal networks using EEG mapping techniques", NeuroImage, Vol. 42, pp. 591-602, February 2008

Non-patent Reference 3: S. Ogawa, T. M. Lee, A. R. Kay, and D. W. Tank, "Brain magnetic resonance imaging with contrast dependent on blood oxygenation", Proc. Natl. Acad. Sci. USA., Vol. 87, No. 24, pp. 9868-9872, December 1990

Non-patent Reference 4: P. Tallgren, S. Vanhatalo, K. Kaila, J. Voipio, "Evaluation of commercially available electrodes and gels for recording of slow EEG potentials", Clinical Neurophysiology, Vol. 116, pp. 799-806, 2005

SUMMARY OF THE INVENTION

Problem to be Solved by the Invention

Patent References 3 and 4 disclose EEG measurement techniques, but no description is given regarding the electrode structure for detecting as many EEG signals as possible from the fitting surface such as limited brain surface of small animals.

In view of the problem described above, a purpose of the present invention is to provide an electroencephalogram electrode unit for small animals and a measurement system using the same for detecting as many EEG signals as possible from the limited brain surface space of small animals.

Means for Solving Problem

To achieve the above objective, an electroencephalogram electrode unit for small animals in a first embodiment of the present invention includes: a base that covers the scalp or brain surface of a small animal and has a plurality of through holes; and a plurality of electrodes, characterized in that: each of the plurality of electrodes is inserted into the plurality of through holes; each of the plurality of electrodes has an insulating tube, an electrode section disposed within the tube, an extraction conducting wire that is connected to the electrode section and that extracts electroencephalogram signals to the exterior, and a paste that is filled within the tube; the tube is installed in the through hole in a manner of standing upright from the scalp or brain surface; and the electrode section is formed in the form of a wire and is disposed, in a manner of standing upright from the scalp or brain surface, within the paste filled within the tube.

To achieve the above objective, an electroencephalogram electrode unit for small animals in a second embodiment of the present invention includes: a base that covers the scalp or brain surface of a small animal and has a plurality of through holes; and a plurality of electrodes, characterized in that: each of the plurality of electrodes is inserted into each of the plurality of through holes; each of the plurality of electrodes is equipped with an insulating inner first tube, an insulating outer second tube for housing the first tube, an electrode section installed within the first tube, an extraction conducting wire that is connected to the electrode section and extracts electroencephalogram signals to the exterior, and a paste that is filled within the tube; the first tube and the second tube are installed in the through hole in a manner of standing upright from the scalp or brain surface; and the electrode section is formed in the form of a wire and is disposed, in a manner of standing upright from the scalp or brain surface, within the paste filled within the first tube.

In the above embodiment, the tube is preferably inserted in order that it can be moved along the axial direction of the through holes. Furthermore, the bottom edge and the side surface of the electrode section contact to the paste.

On the outside of the tube, an outer tube to be fixed to the through hole of the base may be further installed, while the inner tube may be inserted in order that it can be moved along the axial direction of the outer tube.

The electrolyzable paste is preferably a mixture of a paste for electroencephalogram and a physiological saline solution.

The base is further equipped with an opening, into which an electrode for intracranial measurement is inserted.

The tube is preferably equipped with optical fibers.

To achieve the above objective, an electroencephalogram measurement system, simultaneous electroencephalogram and f-MRI measurement system, simultaneous electroencephalogram and NIRS measurement system, simultaneous electroencephalogram, f-MRI and NIRS measurement system, and simultaneous electroencephalogram and intracranial measurement system in a third embodiment of the present invention are characterized in that the electroencephalogram electrode unit for small animals described above is used.

Furthermore, it is preferable that the above measurement system be capable of performing electrocardiographic measurement simultaneously.

Effects of the Invention

According to the electroencephalogram electrode unit for small animals of the present invention, the area of the metallic part of the electrode can be minimized, and thus the number of electrodes for electroencephalogram measurement can be increased easily.

By using the electroencephalogram electrode unit for small animals of the present invention, not only electroencephalogram measurement of small animals but also MRI measurement, f-MRI measurement, electrocardiographic measurement (ECG measurement), near infrared spectroscopy (NIRS), and intracranial measurement can be performed simultaneously.

MODE FOR CARRYING OUT THE INVENTION

Figure 1:
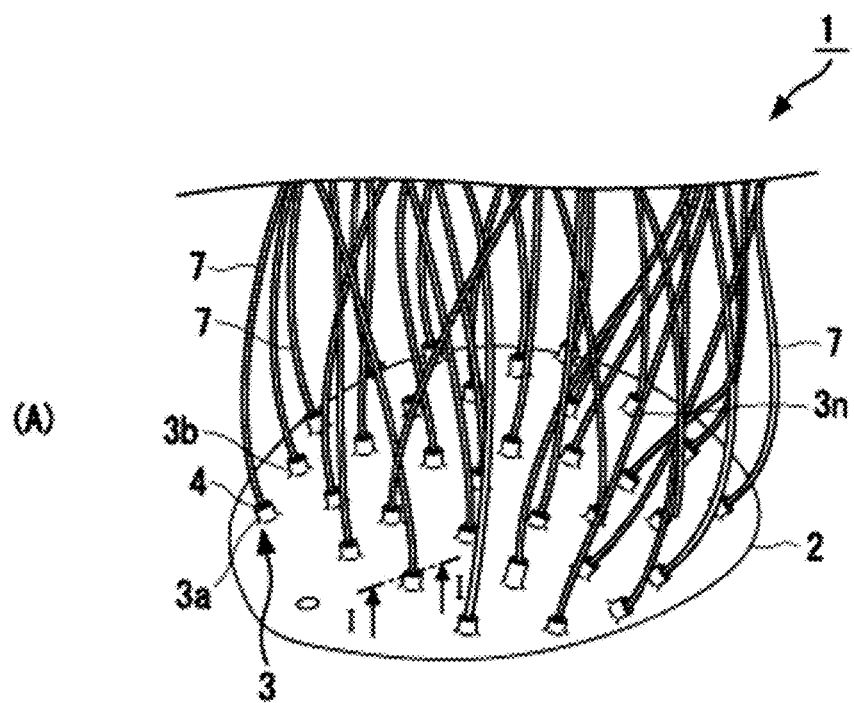
FIG. 1 shows the structure of an electroencephalogram electrode unit for small animals in a first embodiment of the present invention, wherein (A) is an oblique perspective view and (B) is a cross-sectional view along the line I-I in (A)
Figure 1:
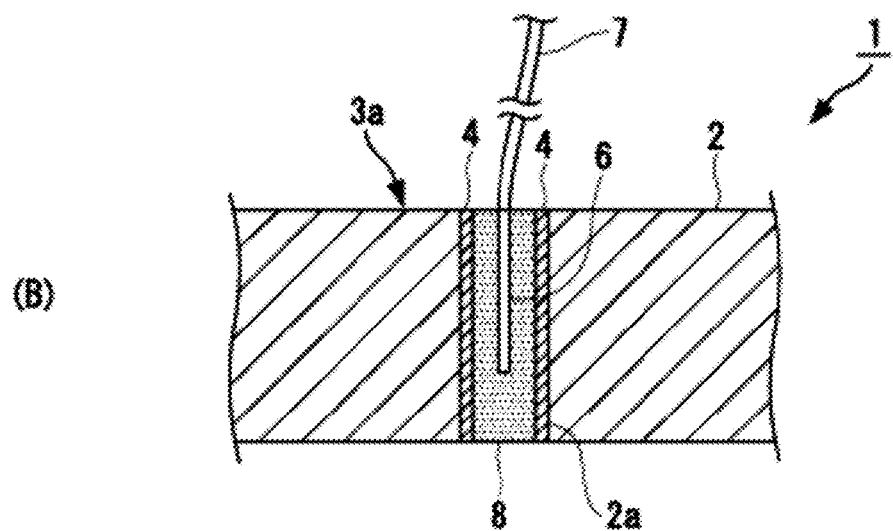

Embodiments of the present invention will hereinafter be described in detail by referring to the drawings.
(First Embodiment)

As a first embodiment, an electroencephalogram electrode unit for small animals will be described.

FIG. 1 shows the structure of the electroencephalogram electrode unit for small animals of a first embodiment of the present invention, wherein (A) is an oblique perspective view and (B) is a cross-sectional view along the line I-I in (A).

As shown in FIG. 1, the electroencephalogram electrode unit 1 for small animals of the present invention includes: a base 2 that covers the scalp of a small animal and has a plurality of through holes 2a; and a plurality of electrodes 3 (3a to 3n). Each of the plurality of electrodes is inserted into each of the plurality of through holes 2a. Each of the plurality of electrodes 3 is equipped with an insulating tube 4, an electrode section 6 installed within the tube 4, an extraction conducting wire 7 that is connected to the electrode section 6 and extracts electroencephalogram signals to the exterior, and a paste 8 that is filled within the tube 4.

It is required that the base 2 is made of a material that is not magnetized and hence is compatible with MRI and f-MRI and whose shape can be changed freely according to the shape of the scalp or brain surface of a small animal. As a material for the base 2, a resin can be used. The length of the through hole 2a in the axial direction is approximately the same as the thickness of the base 2, falling with a range from 1 mm to 5 mm, for example. The length of the tube 4 in the axial direction falls within a range from 5 mm to 2 cm, for example.

The outer diameter of the tube 4 is slightly larger than the diameter of the through hole disposed on the base 2. The difference in these dimensions is approximately 0.01 to 0.1 mm. Consequently, the tube 4 can be moved along the axial direction of the through hole 2a within the through hole 2a formed on the base 2. It is desirable that the base 2 and the tube 4 is made of a material that can be handled easily while they have high coefficient of dynamic friction (µ), such as polyethylene tube, for example. It is only necessary that the coefficient of dynamic friction µ is set within a range from 0.05 to 0.4, for example.

(Variation 1 of the First Embodiment)

Figure 2:
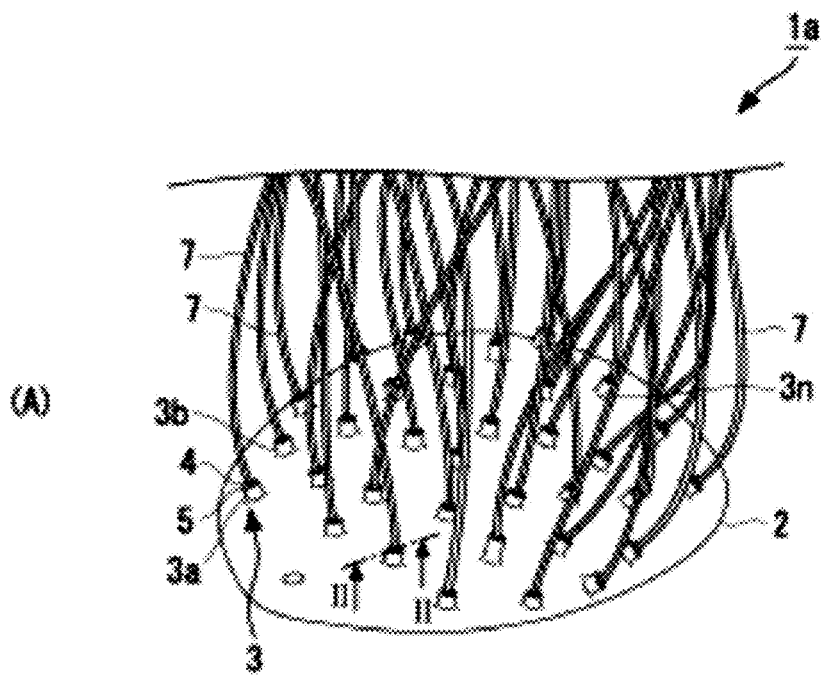
FIG. 2 shows the structure of variation 1 of the electroencephalogram electrode unit for small animals of the first embodiment of the present invention, wherein (A) is an oblique perspective view and (B) is a cross-sectional view along the line II-II in (A)
Figure 2:
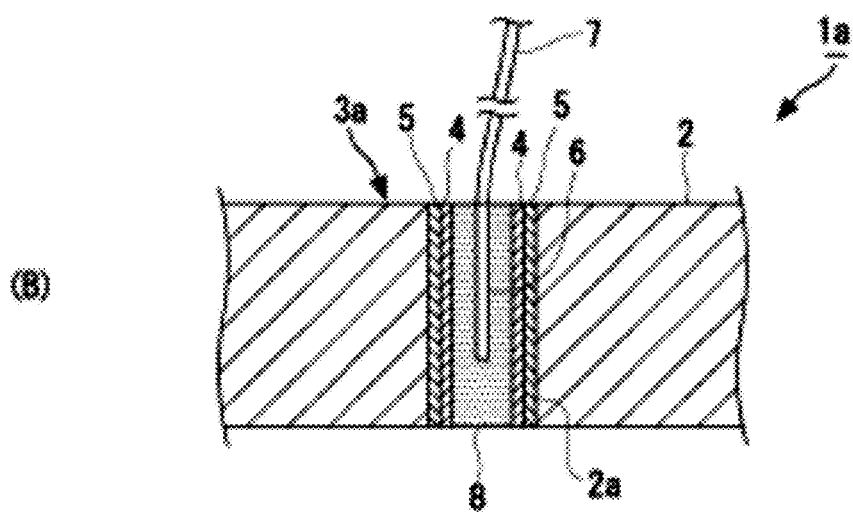

FIG. 2 shows the structure of variation 1 of the electroencephalogram electrode unit for small animals of the first embodiment of the present invention, wherein (A) is an oblique perspective view and (B) is a cross-sectional view along the line II-II in (A).

As shown in FIG. 2 (A), the electroencephalogram electrode unit 1a of the present invention includes: a base 2 that covers the scalp of a small animal and has a plurality of through holes 2a; and a plurality of electrodes 3 (3a to 3n) that are inserted into each of the plurality of through holes 2a. The electroencephalogram electrode unit 1a has a structure with a tube 5 further added to the tube 4 of the electroencephalogram electrode unit 1. The base 2 serves as a foundation to which the outside of the tube 5 is fastened. The inner tube 4 is also called a first tube, whereas outer tube 5 is also called a second tube.

As shown in FIG. 2 (B), the structure of the electroencephalogram electrode unit 1a, wherein an electrode section 6, an extraction conducting wire 7 that is connected to the electrode section 6, and a paste 8 that is filled within the inner first tube 4 are disposed in the inner first tube 4, is the same as the electroencephalogram electrode unit 1.

Figure 3:
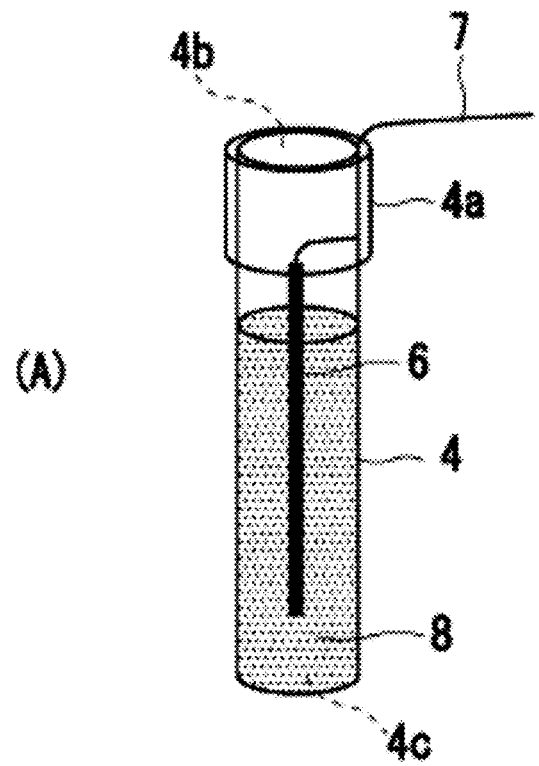
FIG. 3 shows a tube used for variation 1 of the electroencephalogram electrode unit for small animals, wherein (A) shows a first tube and (B) shows a second tube.
Figure 3:
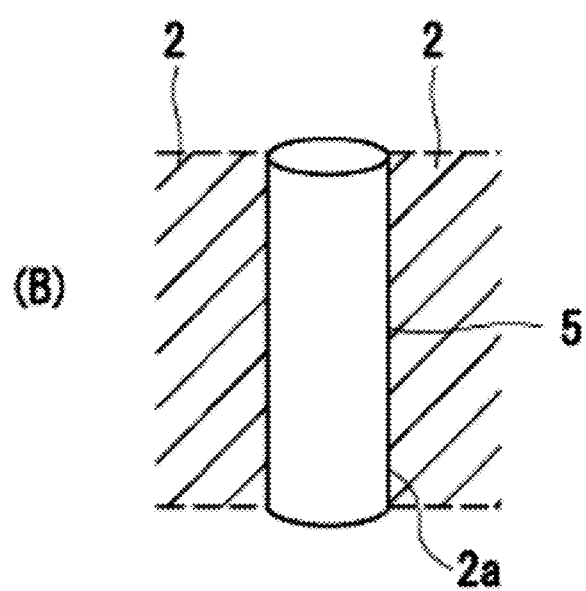

FIG. 3 shows the first tube 4 and the second tube 5 that are used for the electroencephalogram electrode unit 1a for small animals. FIG. 3 (A) shows the first tube 4, whereas FIG. 3 (B) shows the second tube 5. As shown in FIG. 3 (A), the extraction conducting wire 7 may be fastened to the cap 4a of the first tube 4 within the first tube 4. The cap 4a closes the top opening 4b of the first tube 4, from which the extraction conducting wire 7 is extracted. As shown in FIG. 3 (B), the outer periphery of the second tube 5 is inserted into the through hole 2a formed in the base 2, and fastened to the base 2 with an adhesive material, etc. For example, the second tube 5 is provided in a manner where the axis of the tube 5 is perpendicular to the brain surface, with the error range being approximately ±15°. To fasten the first tube 4 within the second tube 5, the inner diameter of the second tube 5 is approximately the same as the outer diameter of the first tube 4, and the outer diameter of the first tube 4 is slightly smaller than the inner diameter of the second tube 5, for example. The difference in these dimensions falls within a range approximately from 0.01 to 0.1 mm. The diameter of the first tube 4 is selected from a range from 1 mm to 5 mm, whereas the diameter of the second tube 5 is selected from a range from 1.1 mm to 5.1 mm.

The length of the first tube 4 falls within a range from 5 mm to 2 cm, for example. The length of the second tube 5 is approximately the same as the length of the through holes 2a of the base 2, 1 mm to 5 mm, for example. Note that FIG. 2 (B) shows an example where the length of the first tube 4 and that of the second tube 5 are equal.

Consequently, the first tube 4 can be moved in the axial direction of the second tube within the second tube 5. It is desirable that these first tube 4 and second tube 5 is made of a material that can be handled easily whereas they have high coefficient of dynamic friction µ. It is only necessary that the coefficient of dynamic friction µ falls within a range from approximately 0.05 to 0.4. These materials include a polyethylene tube, for example. Specifically, cylindrical polyethylene tubes can be used as the first and the second tubes 4, 5.

The electrode section 6 is in a long and thin, i.e. elongated shape, specifically in a form of a wire as shown in the example. The length of the electrode section 6 can fall within a range from 5 mm to 2 cm. The diameter of the electrode section 6 can fall within a range from 0.1 mm to 3 mm. A metallic material used for the electrode section 6 must have high conductivity and excellent electrolytic property. As a material for the electrode section 6, platinum, gold, silver, stainless steel, iridium, tin, etc. can be used (See Non-patent Reference 4.).

The surface area of the electrode section 6 must be large enough to ensure the solid-liquid interface of electrolytic reaction between the electrode section 6 and the paste 8. The surface area may fall within a range from 1.6 mm$^2$ to 30 mm$^2$, for example. This area range is approximately equivalent to the dish-shaped electrode for electroencephalogram measurement (also called EEG) normally used for humans, and can maintain the impedance generated between the scalp and the electrode section 6 as low as possible. One electrode section 6 is disposed for one electrode 3, and approximately 10 to 40 electrode sections are provided over the entire base 2 but the number of electrode sections 6 is not limited to these.

The extraction conducting wire 7 that connects the electrode section 6 and an amplifier for electroencephalogram signals (also called EEG signals) measurement, which will be described later, may be of any materials provided that it has small electrical resistance. Metallic materials and conductive plastic materials may be used. As metallic material 6, copper, bronze gold, silver, platinum, aluminum, etc. can be used.

When a plurality of extracting conductive wires 7 are used, each extraction conductive wire 7 may be covered with an insulating material or a tube made of an insulating material. Consequently each extraction conductive wire 7 can be prevented from contacting each other, thus resulting in short circuit. As a tube of an insulating material, a vinyl tube may be used. A so-called vinyl wire may also be used as such extraction conductive wire 7.

The first tube 4 is filled with an electrolytic paste 8. This paste 9 has conductivity of 0.01 to 10 s/m. Furthermore, the paste 8 must have semi-solid property in order to be poured into the first tube 4. The viscosity can be selected from a range from 2,000 to 10,000 Pa·s. As such a paste 8, a mixture of commercially available electroencephalogram paste (also called EEG paste) and a physiological saline solution can be used. Table 1 lists commercially available standard EEG pastes. For example, an electrolytic paste formed by mixing Biotach (GE Maequette Medical System) and salt water at a volume ratio of 2:1 may be used.

TABLE 1

Commercially available EEG paste

| Trade name | Name of manufacturer |
| --- | --- |
| Biotach | GE Maequette Medical |
| Signa Gel | Parker Laboratories |
| Spectra 360 | |
| Elektrodipasta comp | Berner |
| Ten20 | D.O. Weaver |
| Electro-Gel | Electro-Cap International |
| EC2 | Grass Astro-Med |
| Electrode Jelly | Rochester Electro-Medical |
| Abralyt 2000 | EASYCAP |
| Abralyt HiCl | |

The electrode section 6 in the electroencephalogram electrode unit 1, 1a for small animals of the present invention is surrounded by the paste 8 within the first tube 4. The surface of 1.6 mm$^2$ to 30 mm$^2$ in area including the surface of the cylinder of the electrode section 6 described above contacts to the paste 8. In the example as shown in the figure, the electrode section 6 is embedded in the paste 8 filled within the first tube 4, and the bottom edge and cylindrical side surface of the electrode 6 contact the paste 8. Furthermore, the paste 8 filled within the first tube 4 fills the opening 4c (FIG. 3 (B)) at the bottom end of the relevant tube 4, or the surrounding area of the opening, thereby allowing contact with the brain surface, etc. of small animals. Consequently, electrical resistance between the contact surface of the electrode section 6 and the brain surface of small animals, namely the measurement surface, can be maintained as low as possible.

When the electrode section 6 is made to be long and thin as described above, the contact surface between the electrode section 6 and the electrolytic paste 8 can be increased. In addition, the length and diameter of the electrode section 6 can be selected in order to satisfy required performances of electroencephalogram measurement. When the conductivity of the paste 8 falls within a range from 0.01 S/m to 10 S/m, the electrical resistance between the electrode section 6 and the measurement surface on the brain surface of the small animal, namely impedance, can be made to be as small as 50 kΩ or lower, for example.

To decrease electrical resistance, it may be required to treat the brain surface of a small animal before starting electroencephalogram measurement. When measurement is to be made on the scalp, it is only necessary to shave the hair of the small animal carefully, and to remove oil and grease using an organic solvent such as alcohol. When the measurement is to be made on the skull, a paste having the same conductivity as the scalp is applied to the skull.

The conductive paste 8 must be injected only into the inner first tube 4. The conductive paste 8 can be injected into the inner first tube 4 using an injection syringe. To prevent short circuit between adjacent electrodes caused by the conductive paste 8, the conductive paste 8 must be prevented from running over the first tube 4, spreading over the brain surface of the small animal.

With the electroencephalogram electrode unit 1, 1a for small animals of the present invention, the methods of fastening the back side of the base 2 to the brain surface of the small animal include fastening using a rubber band, surgical stitching, and bonding using dental cement. Fastening methods other than those can also be selected arbitrarily in accordance with the situation of electroencephalogram measurement.

(Variation 2 of the First Embodiment)

As variation 2 of the first embodiment of the present invention, electroencephalogram electrode unit 1b for small animals will be described.

Figure 4:
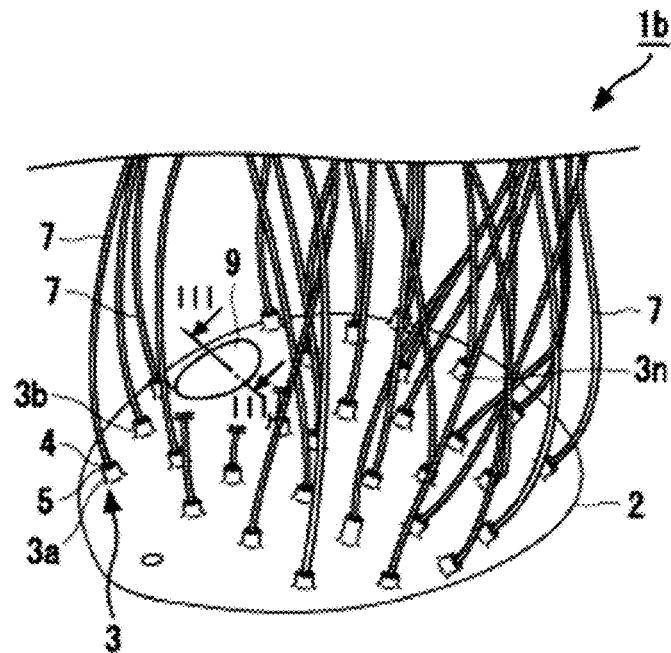
FIG. 4 shows the structure of variation 2 of the electroencephalogram electrode unit for small animals in the first embodiment of the present invention, wherein (A) is an oblique perspective view and (B) is a cross-sectional view along the line III-III in (A)
Figure 4:
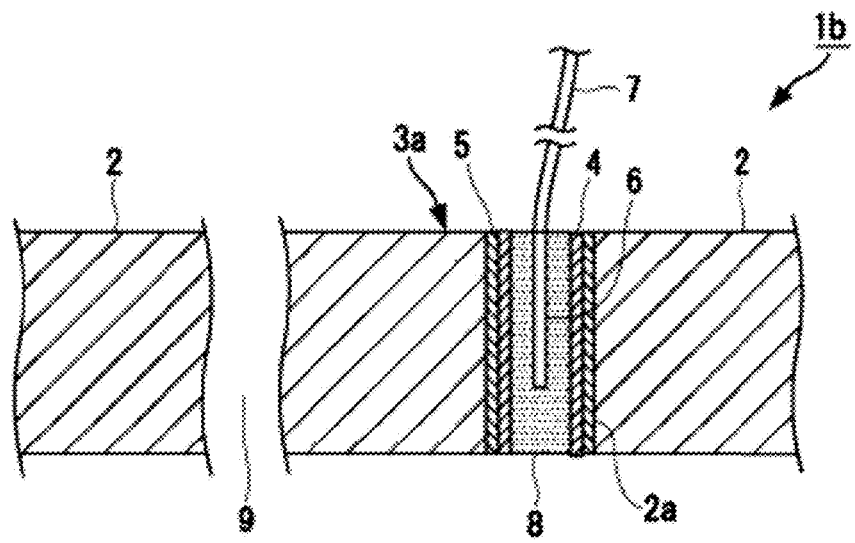

FIG. 4 shows the structure of electroencephalogram electrode unit 1b for small animals of variation 2 of the first embodiment of the present invention, wherein (A) is an oblique perspective view and (B) is a cross-sectional view along the line III-III in (A).

As shown in FIG. 4 (A), the electroencephalogram electrode unit 1b for small animals of the present invention has a structure with an opening 9 added to the base 2 of the electroencephalogram electrode unit 1a as shown in FIG. 3. As shown in FIG. 4 (B), the opening 9 has a hole structure penetrating from the surface to the back face of the base 2. This opening 9 can be used as a hole into which an intracranial measurement electrode for intracranial electroencephalogram measurement, which will be described later, is inserted. The opening 9 can be not only in a circular shape but also in U-shape cutting from the outermost periphery of the base 2 into inside of the base 2.

Consequently, with the electroencephalogram electrode unit 1, 1a, 1b for small animals of the present invention, the electrical resistance between the electrode section 6 and the measurement surface of the brain of the small animal can be maintained as low as possible by enclosing the electrode section 6, which is highly conductive metallic wire, with the resin first tube 4, and filling the tube 4 with electrolytic paste 8, thereby increasing the contact surface between the electrode section 6 and the electrolytic paste 8.

According to the electroencephalogram electrode unit 1, 1a, and 1b for small animals of the present invention, since the electrode section 6 in a shape of a wire is held in the base 2, standing upright from the brain surface, the area of the metallic portion of the electrode section 6 facing opposite to the brain surface can be maintained minimal. And, a plurality of electrodes, namely a plurality of channels, can be installed in the electroencephalogram electrode unit 1, 1a, and 1b quite easily.

Consequently, according to the electroencephalogram electrode unit 1, 1a, 1b for small animals of the present invention, a plurality of electrodes, 32 channels for example, can be achieved. With conventional electroencephalogram measurement of small animals, metallic electrode on the brain or scalp, or carbon electrode is placed directly on the brain surface of a small animal and fastened. Compared with the conventional method, wherein the number of electrodes was extremely small since the electrodes were fastened in this way, the electroencephalogram electrode unit 1, 1a, 1b for small animals of the present invention allows multi-channel electroencephalogram measurement of small animals to be conducted. Furthermore, simultaneous measurement of electroencephalogram and f-MRI or NIRS as well as simultaneous measurement of electroencephalogram and intracranial measurement of electroencephalogram can also be realized.

According to the electroencephalogram electrode unit 1b for small animals of the present invention, the intracranial electroencephalogram measurement, namely the electroencephalogram measurement within a cranium, can be performed by inserting the electrode for intracranial measurement into the opening 9. It is therefore possible to perform electroencephalogram measurement on the scalp and within the cranium simultaneously according to the electroencephalogram electrode unit 1b for small animals.

(Second Embodiment)

As a second embodiment of the present invention, an electroencephalogram measurement system using the electroencephalogram electrode unit 1 for small animals will be described. The electroencephalogram measurement system using the electroencephalogram electrode unit 1a will be described below. However the electroencephalogram electrode unit 1, 1b can also be applied to the electroencephalogram measurement system.

The electroencephalogram measurement system in the second embodiment can be constructed using electroencephalogram electrode unit 1a for small animals of the present invention and the commercially available electroencephalogram measurement equipment for humans. Namely, the electroencephalogram of small animals can be measured easily by placing the electroencephalogram electrode unit 1a for small animals of the present invention onto the brain or head of a small animal, and inputting electroencephalogram signals from the electroencephalogram electrode unit 1a into the commercially available electroencephalogram measurement equipment for humans.

Figure 5:
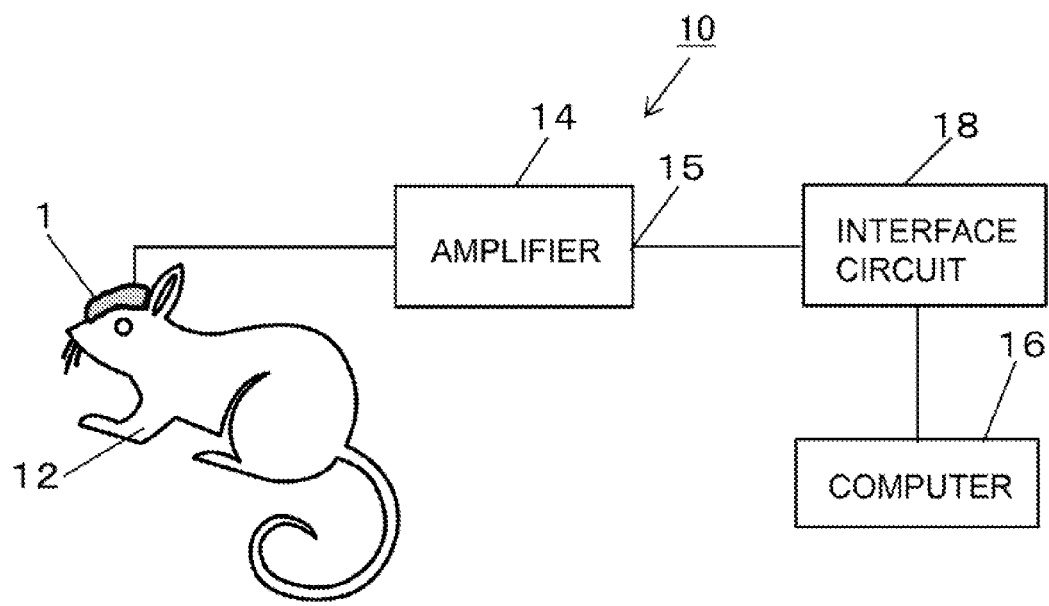
FIG. 5 is a schematic block diagram showing a typical structure of an electroencephalogram measurement system using the electroencephalogram electrode unit for small animals in a second embodiment of the present invention.

FIG. 5 is a schematic block diagram showing a typical structure of an electroencephalogram measurement system 100 related to the second embodiment of the present invention. The electroencephalogram measurement system 100 is provided with the electroencephalogram electrode unit 1a and electroencephalogram measuring equipment 10.

As shown in FIG. 5, the electroencephalogram measurement device 10 includes an amplifier 14 allowing multi-channel inputs of electroencephalogram signals from the electroencephalogram electrode unit 1a for small animals mounted to the head of a small animal 12 to be measured, a computer 16, and an interphase circuit 18 for inputting the output signals 15 from this amplifier 14 into the computer 16. As the computer 16, a personal computer, etc. can be used. The interface circuit 18 is an A/D converter, for example.

According to the encephalogram electrode unit 1a for small animals of the present invention, the electrical resistance between the electrode section 6 and the measurement surface of the brain of the small animal 12 can be maintained as low as possible. The electrode section 6 for electroencephalogram measurement can be made to have a plurality of electrodes easily.

According to the electroencephalogram electrode unit 1a for small animals of the present invention, two cylindrical tubes having different outer diameters, namely a first tube 4 and a second tube 5 (each of them may hereafter be referred to as the tube) are used. The outer second tube 5 is fastened to the wall of the through hole 2a of the base 2, and the inner cylindrical tube 4 is inserted into the outer tube 5 in a state movable in the axial direction. The inner tube 4 containing the electrode section 6 can therefore be made to contact the scalp in the vertical direction with respect to the scalp. Consequently, even if the small animal 12 should move during electroencephalogram measurement, the inner tube 4, whose bottom opening 4c (FIG. 3 (a)) is made to contact the brain surface, moves against the outer tube in response to the movement of the small animal. Therefore the stable electroencephalogram measurement can be performed. This ensures efficient electroencephalogram measurement of the small animal 12.

(Variation of the Second Embodiment)

As a variation of the second embodiment of the present invention, a measuring equipment 10a, namely an electroencephalogram (EEG) measurement system using the electroencephalogram electrode unit for small animals equipped with an electrocardiogram (ECG) measurement system, will be described.

Figure 6:
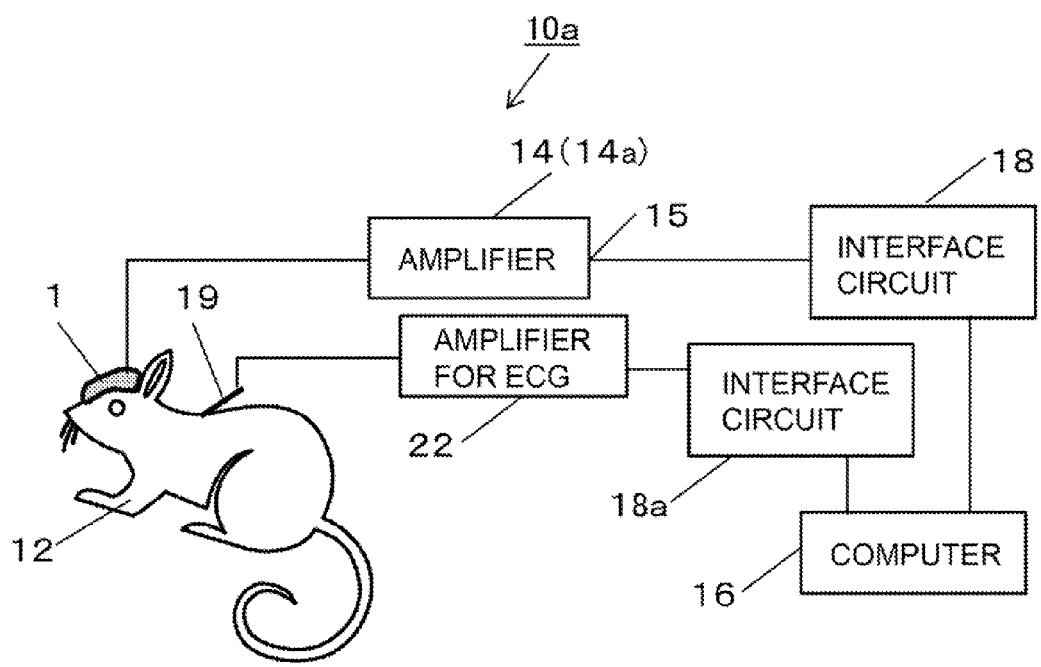
FIG. 6 is a schematic block diagram showing a typical structure of an electroencephalogram measurement system using the electroencephalogram electrode unit for small animals in a variation of the second embodiment of the present invention.

FIG. 6 is a schematic block diagram showing a typical structure of the electroencephalogram measuring equipment 10a using the electroencephalogram electrode unit 1a for small animals related to the variation of the second embodiment of the present invention. Needless to say, electroencephalogram electrode units 1, 1b can be used instead of the electroencephalogram electrode unit 1a.

The electroencephalogram measuring equipment 10a as shown in FIG. 6 is different from the electroencephalogram measuring equipment 10 as shown in FIG. 5. The difference is that the electroencephalogram measuring equipment 10a is further provided with: an amplifier 22 for electrocardiogram measurement (also called ECG measurement) for amplifying signals from the electroencephalogram electrode unit 19 mounted to the small animal 12; and an interphase circuit 18a for inputting the signals from this amplifier 22 for ECG into the personal computer 16. For example, the interface circuit 18a is an A/D converter. When the amplifier 14 for electroencephalogram measurement is an amplifier having multi-channel inputs, signals from the electrode 19 for electrocardiogram measurement may be input into the amplifier 14a capable of multi-channel inputs. Then, signals from the electrode 19 may be output to the interface circuit 18.

According to the electroencephalogram measuring equipment 10a in FIG. 6, the signals from the brain and the heart of the small animal 12 can be measured with time. In this case, noise due to signals from the heart mixing into brain signals, namely so-called ballisto-cardiogram artifact, can be prevented efficiently.

The ballisto-cardiogram artifact is removed by performing arithmetic processing by the personal computer 16, with using cyclic electrocardiogram signals (ECG signals) as reference signals, for example.

A method of manufacturing electroencephalogram electrode unit 1, 1a, and 1b will hereinafter be described. (Manufacturing method of the base 2 of electroencephalogram electrode unit 1)

(1) A drawing of the base 2 of a desired shape is made.
(2) A mold is created using clay.
(3) A thermoplastic resin is inserted into the mold to fabricate the base 2.
(4) The resin is taken out of the mold, and lastly the shape of the resin is adjusted.

(Manufacturing Method of the Base 2 of Electroencephalogram Electrode Unit 1a)

In the case of electroencephalogram electrode unit 1a, the second tube 5 is inserted into the through hole 2a of the base 2, and fastened using an adhesive agent, etc. As the second tube 5, a polyethylene tube was used as an example. The internal diameter of the second tube 5 was 1.4 mm, its outer diameter was 1.6 mm, and its length was 6 mm.

(Manufacturing Method of the Base 2 of Electroencephalogram Electrode Unit 1b)

Electroencephalogram electrode unit 1b can be manufactured by making an opening 9, into which an electrode for intracranial measurement is inserted, on the base 2, in addition to the case of electroencephalogram electrode unit 1a.

Figure 7:
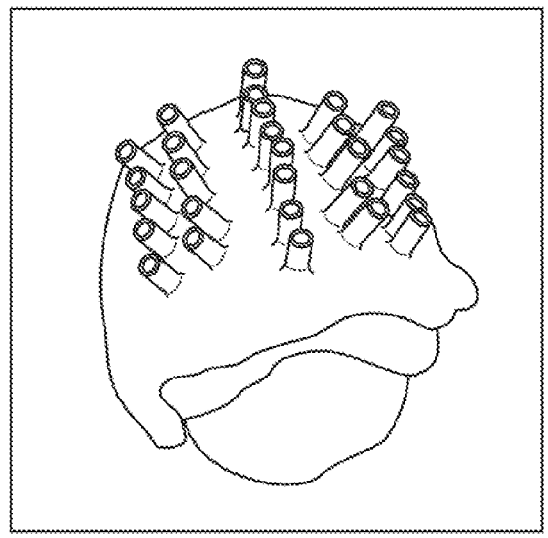
FIG. 7 is an optical image showing the base of the electroencephalogram electrode unit for small animals in the first embodiment of the present invention.

FIG. 7 is an optical image of the base 2 of electroencephalogram electrode unit 1a for small animals in the first embodiment of the present invention. As shown in FIG. 7, the second tube 5 is disposed in each of the through holes 2a of 31 pieces not shown. The resin used as the base 2 is a resin compatible with MRI (for example, HB-100S-B1, Taiyo Electric Ind. Co., Ltd).

(Manufacturing Method of the Electrode Section 6 of Electroencephalogram Electrode Unit 1)

(1) A drawing of the electrode section 6 of a desired shape is made, and the electrode section 6 is manufactured.

A platinum wire was used as the electrode section 6. Typical dimensions were as follows: diameter; 0.3 mm, length; 0.8 mm, and surface area; 7.67 mm$^2$, respectively.

(2) The metallic part of the electrode section 6 and the extraction conducting wire 7 are soldered.

(3) The extraction conducting wire 7 is fastened to the amplifier 14 for signals.

(4) The electrode section 6 is made to pass through the first tube 4 and fastened.

As the first tube 4, a polyethylene tube was used. The diameter of the tube 4 was 1.33 mm, and its length was 10 mm.

The method of manually manufacturing electroencephalogram electrode unit 1 was described above. However, it is also possible to automatically manufacture the electroencephalogram electrode unit 1 using a commercially available 3D printer. The electrode section 6 of electroencephalogram electrode units 1a, 1b can also be manufactured in the same manner as the electrode section 6 of electroencephalogram electrode unit 1.

Figure 8:
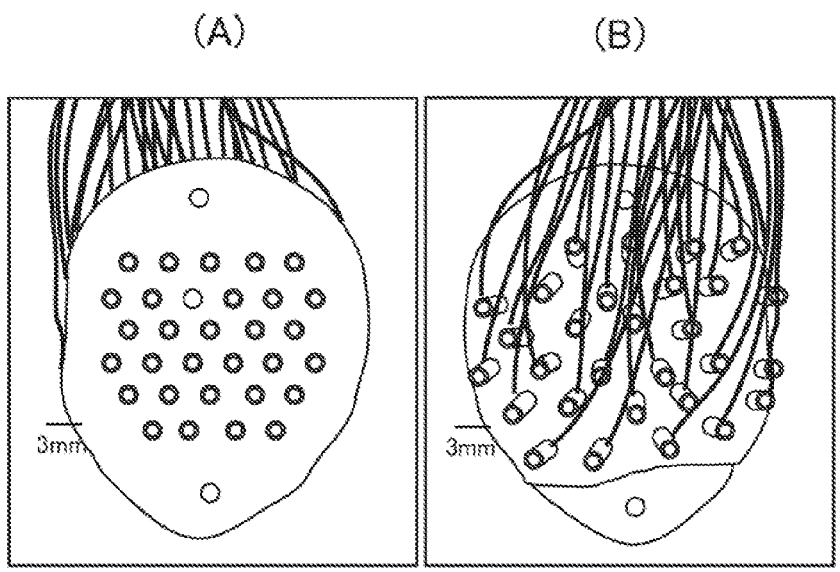
FIG. 8 shows optical images showing the appearance of the electroencephalogram electrode unit for small animals manufactured, wherein (A) shows the surface side and (B) shows the scalp side.

FIG. 8 shows optical images showing the appearance of electroencephalogram electrode unit 1a for small animals manufactured, wherein (A) shows the surface side and (B) shows the scalp side. As shown in FIG. 8, 31 pieces of electrode sections 6 have been formed.

Then the manufactured electroencephalogram electrode unit 1a for small animals was placed on the scalp of a male Wistar rat as a small animal 12 using a rubber band.

Figure 9:
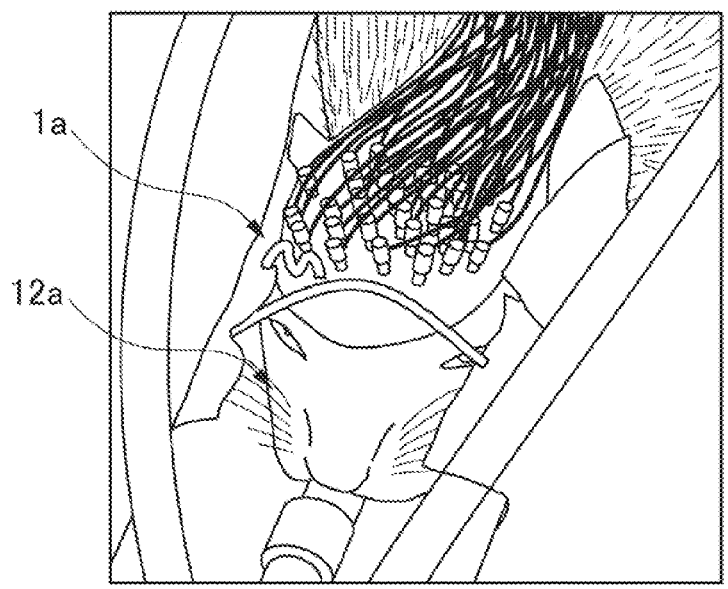
FIG. 9 is an optical image showing the appearance of the electroencephalogram electrode unit for small animals placed on the scalp of a Wistar rat.

FIG. 9 is an optical image showing the appearance of the electroencephalogram electrode unit 1a for small animals placed on the scalp of the Wistar rat 12a. From FIG. 9, it is apparent that the electroencephalogram electrode unit 1a for small animals has an area small enough to be mounted on the head of the Wistar rat 12a.

(Example of Measurement Using the Electroencephalogram and Electrocardiogram Measuring Equipment 10a)

The electroencephalogram and electrocardiogram measuring equipment 10a having a similar structure to the one as shown in FIG. 6 was used. A needle electrode 19 (SA Instruments, USA) was inserted into the right hind paw of the Wistar rat 12a as an ECG electrode. The 31 conductive wires and one ECG electrode from the electroencephalogram electrode unit 1a were connected to A/D converter 18 (USB-6221, National Instruments, USA) via 32-channel battery amplifier 14a (Brain Products, Germany). The A/D converter 18 was controlled using software (data acquisition tool box, MAT-LAB, USA). Electroencephalogram was measured using software for electroencephalogram measurement (Brain-Record, Ver. 1.4, Brain Products, Germany).

The sampling frequency for electroencephalogram measurement was 5000 Hz, the impedance of electrode unit 1a for electroencephalogram measurement for small animals was 50 kΩ or lower, and grounding impedance and reference impedance were 50 kΩ or lower.

Figure 10:
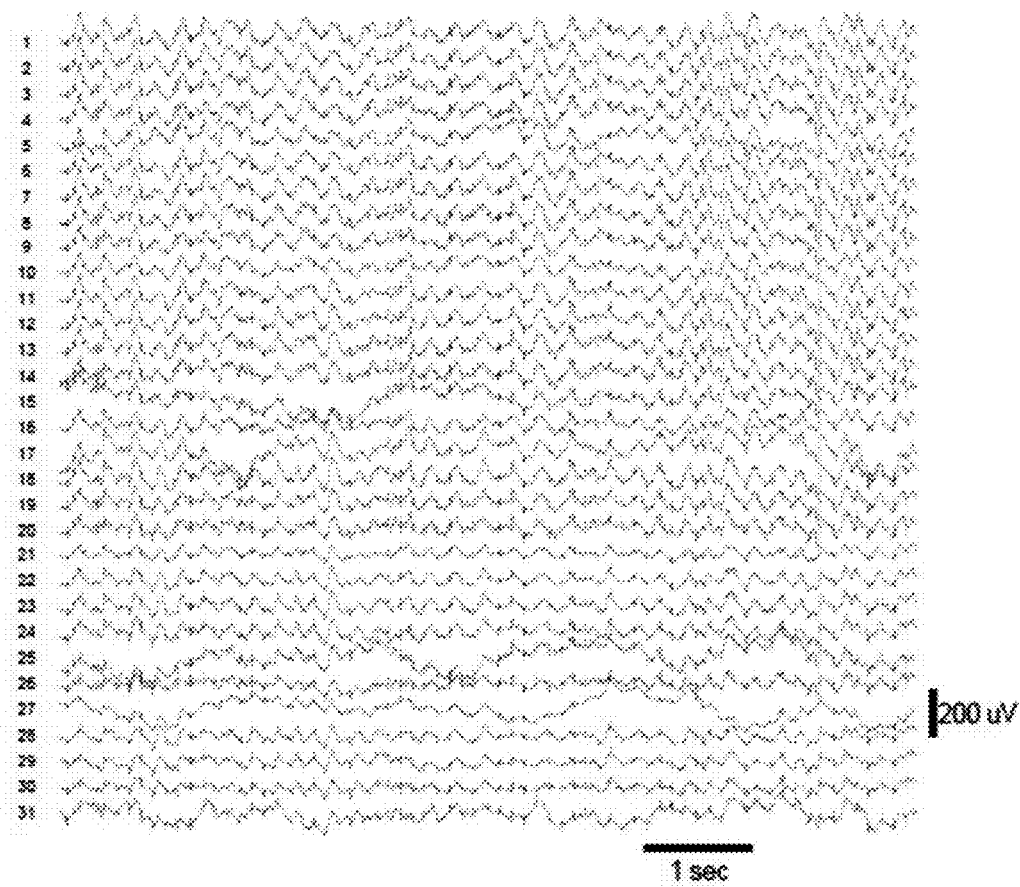
FIG. 10 is a chart showing electroencephalogram measured by using the electroencephalogram electrode unit for small animals manufactured.

FIG. 10 is a chart showing electroencephalogram measured by using the fabricated electroencephalogram electrode unit 1a for small animals. The horizontal axis in FIG. 10 represents time (second), and the vertical axis represents the amplitude (microvolt) of electroencephalogram. As shown in FIG. 10, it is obvious that the electroencephalogram is free from noise, which means that the measurement has been made at high S/N ratio.

(Intracranial Electroencephalogram Measurement)

The intracranial electroencephalogram measurement will then be explained.

By using the electroencephalogram electrode unit 1b for small animals of the present invention, not only electroencephalogram measurement using the electroencephalogram electrode unit 1, 1a placed on the scalp or skull but also intracranial electroencephalogram measurement can be performed. The intracranial electroencephalogram measurement is taken at the bottom of the skull, and is also referred to as intracranial recording.

Figure 11:
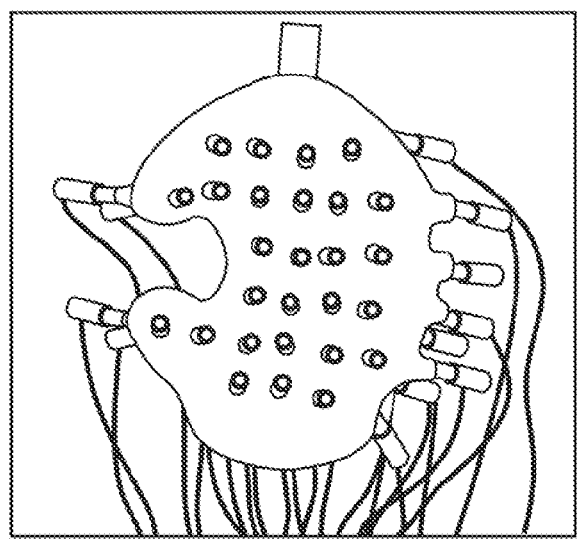
FIG. 11 provides images showing the appearance of the electroencephalogram electrode unit for small animals manufactured, wherein (A) shows the skull side and (B) shows the surface side.
Figure 11:
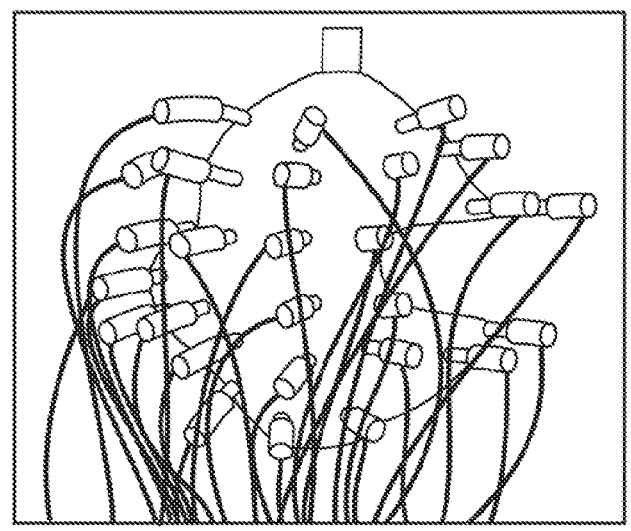

FIG. 11 shows the appearance, etc. of the fabricated electroencephalogram electrode unit 1b for small animals, wherein (A) shows the skull side and (B) shows the surface side.

As shown in FIG. 11, on the electroencephalogram electrode unit 1b for small animals, electrode sections 6 of 27 pieces are formed. Furthermore, to install the electrode section 6 for intracranial recording, an opening 9 is formed in the electroencephalogram electrode unit 1b as shown in FIG. 11 (A). Thereby, it is possible to measure the electroencephalogram on the skull and intracranial recording simultaneously.

Figure 12:
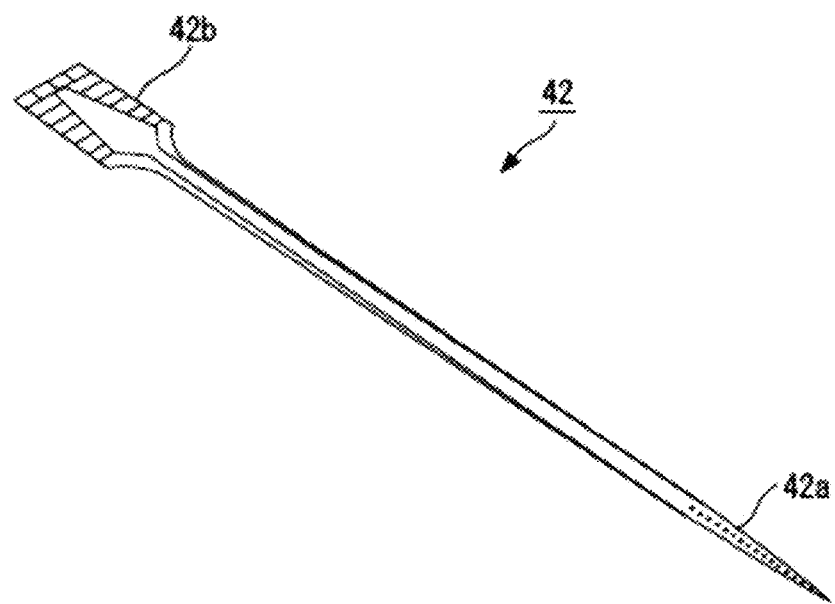
FIG. 12 is a schematic block diagram showing a commercially available electrode for intracranial measurement, wherein (A) is an oblique perspective view and (B) is a magnified plan view of the electrode section.
Figure 12:
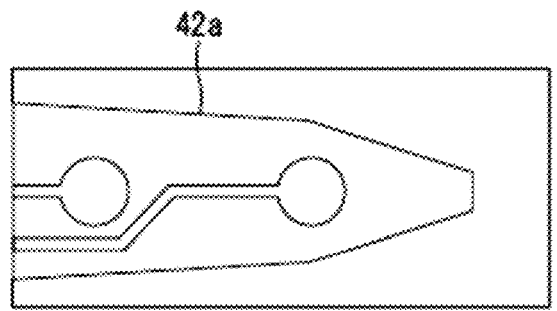

FIG. 12 is a schematic block diagram showing a commercially available electrode for intracranial measurement 42, wherein (A) is an oblique perspective view and (B) is a magnified plan view of the electrode section 42a.

As shown in FIG. 12 (A), one side of the electrode 42 for intracranial recording to be inserted into the opening 9 of the electroencephalogram electrode unit 1b for small animals is in a shape of a wire, and on its edge, electrode section 42a having a given number of channels, 16 channels for example, is formed. The other edge on the top left side of the electrode 42 for intracranial recording is the terminal area 42b of the electrode section 42a. The patterns corresponded to the number of channels of the electrode section 42a, which can be soldered to the printed circuit board, are formed. As shown in FIG. 12 (B), the distance between electrodes 12c provided at the edge of the electrode section 42a is 50 μm, for example. The area of each electrode 12c is approximately 177 μm$^2$, for example.

Figure 13:
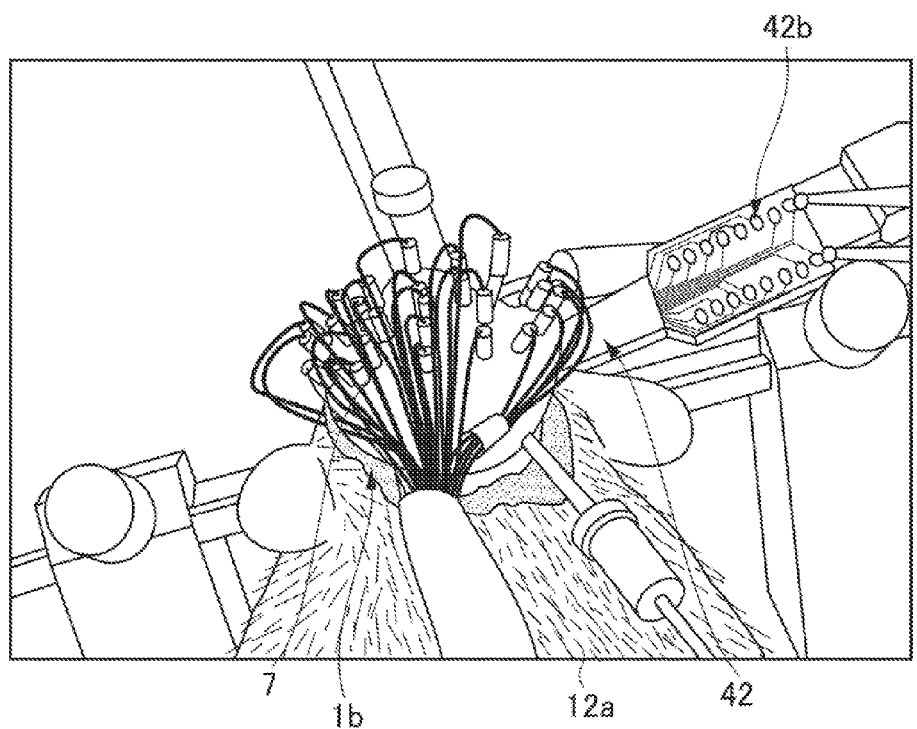
FIG. 13 is an optical image showing the appearance of the electroencephalogram electrode unit for small animals placed on the scalp of a Wistar rat.

FIG. 13 is an optical image showing the appearance of electroencephalogram electrode unit 1b for small animals placed on the scalp of a Wistar rat 12a.

From FIG. 13, it is apparent that an extraction conducting wire 7 is mounted to the Wistar rat 12a, and on the upper right side, an electrode for intracranial recording 42 (a1×16-5 mm-177, NeuroNexus Technologies) is inserted into the skull. The electrode section 42a in a shape having a sharp edge of the electrode for intracranial recording 42 as shown in FIG. 12 is inserted into the brain cortex after making a hole in the skull and peeling the dura matter. The top right part of the electroencephalogram electrode unit 1b shown in FIG. 13 is the terminal area 42b of the electrode 42 for intracranial recording. In this terminal area 42b, 16 ball-shaped soldered layers are formed.

Figure 14:
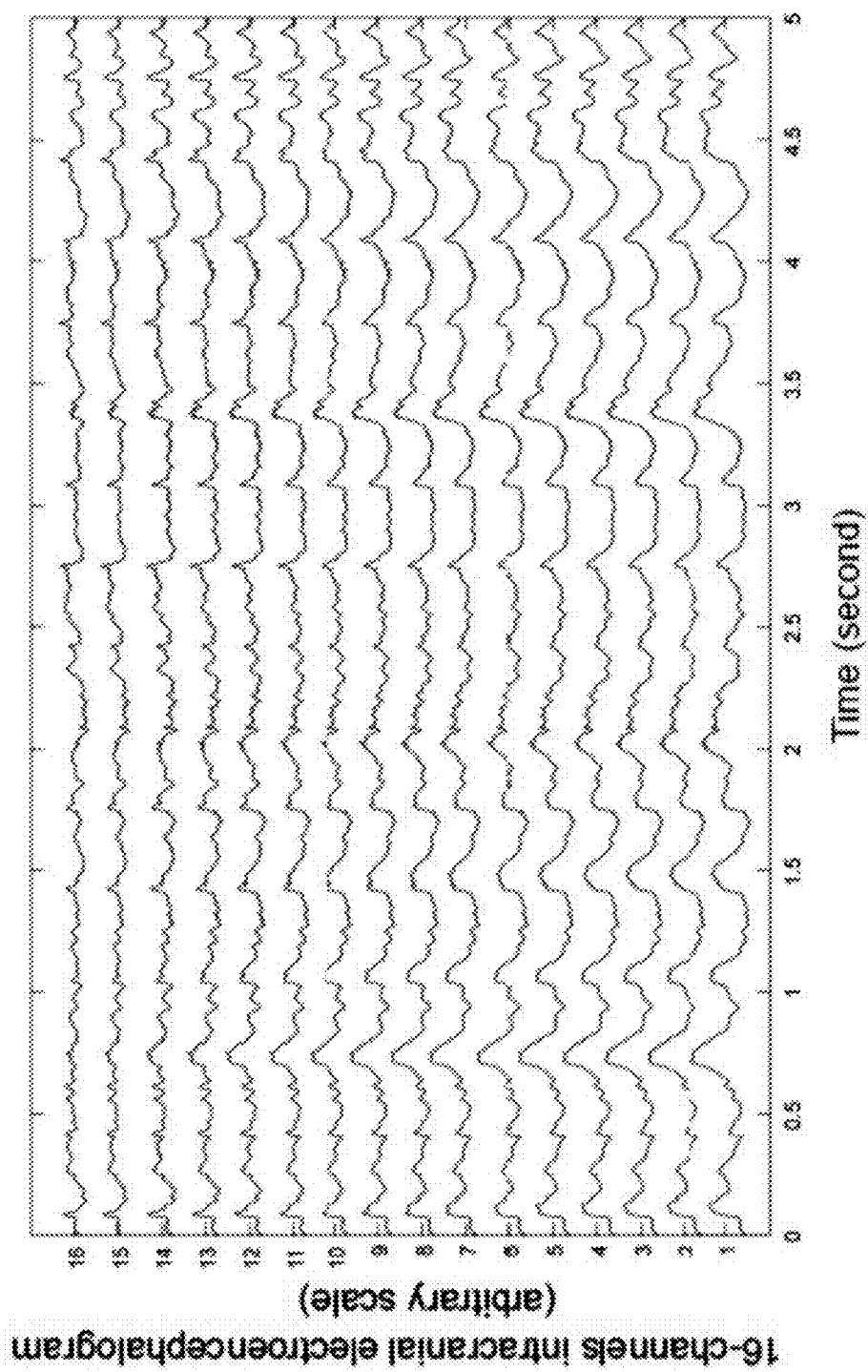
FIG. 14 is a chart showing 16-channel intracranial electroencephalogram measured by the electroencephalogram electrode unit for small animals manufactured.

FIG. 14 is a chart showing 16-channel intracranial electroencephalogram waveforms measured with the electroencephalogram electrode unit 1b for small animals manufactured. The horizontal axis in FIG. 14 represents time (second), and the vertical axis represents 16-channel intracranial electroencephalogram amplitude (arbitrary scale).

As shown in FIG. 14, it is obvious that the intracranial electroencephalogram is free from noise, meaning that the measurement is made at high S/N ratio. Furthermore, the electroencephalogram measured on the scalp was found to be similar to the electroencephalogram measured using the electroencephalogram electrode unit 1a for small animals shown in FIG. 10. From the above, it was found that EEG measurement on the skull could also be performed as in the case where the system was mounted on the scalp. This is a measurement that cannot be achieved conventionally to the best of the present inventor's knowledge.

Consequently, according to the electroencephalogram electrode unit 1b for small animals of the present invention, electroencephalogram measurement on the scalp of a small animal 12 and intracranial measurement can be performed simultaneously.

(Third Embodiment)

As a measurement system using the electroencephalogram electrode unit 1 for small animals in a third embodiment of the present invention, a system capable of performing simultaneous electroencephalogram and f-MRI measurements will be described. In the following description, a measurement system using the electroencephalogram electrode unit 1 will be described, but electroencephalogram electrode units 1a and 1b are also applied by the same manner.

Figure 15:
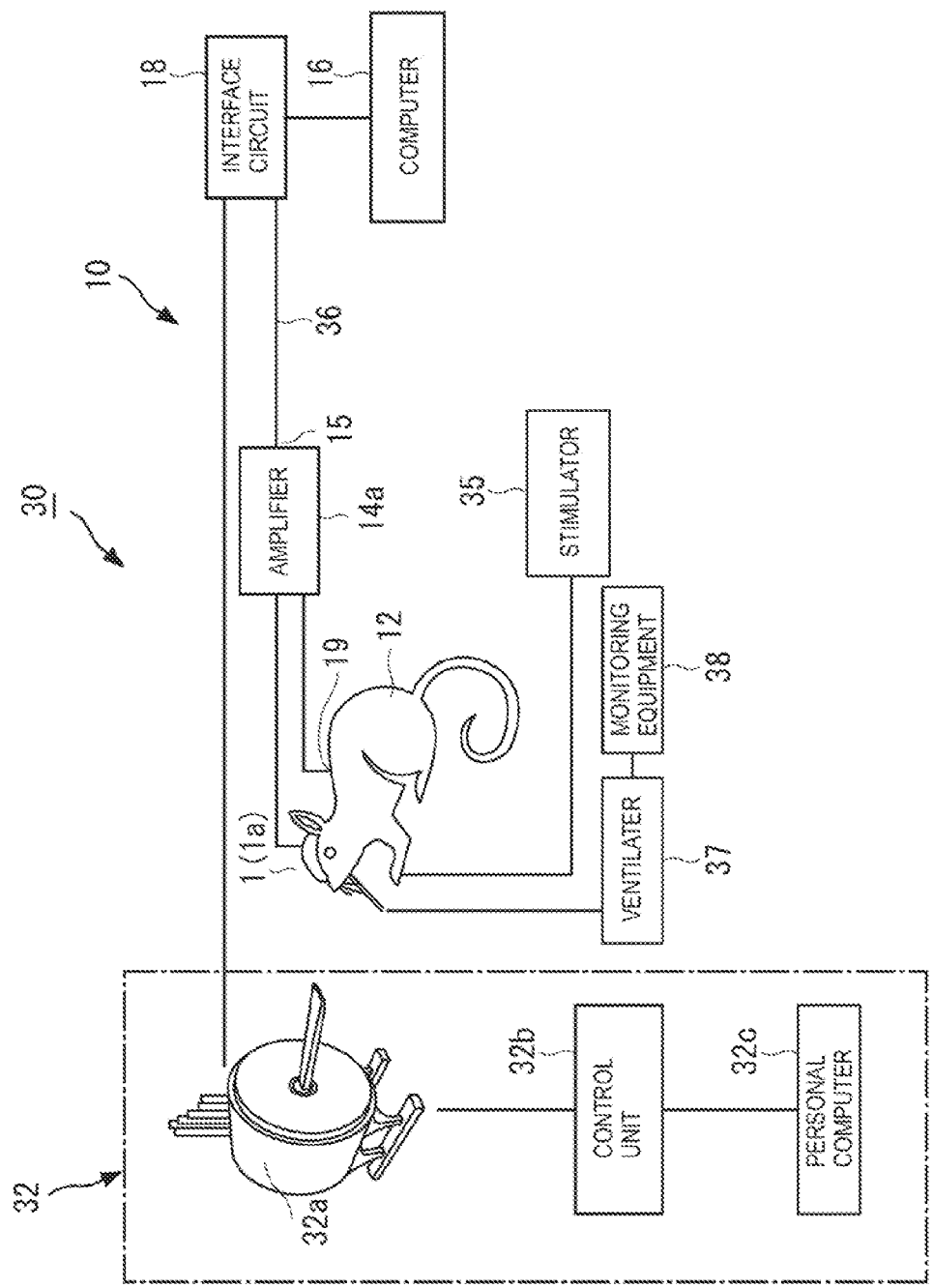
FIG. 15 is a schematic block diagram showing the structure of a simultaneous electroencephalogram and f-MRI measurement system using the electroencephalogram electrode unit for small animals in a third embodiment of the present invention.

FIG. 15 is a schematic block diagram showing the structure of simultaneous electroencephalogram and f-MRI measurement system 200 using the electroencephalogram electrode unit 1 for small animals in a third embodiment of the present invention.

The simultaneous measurement system 200 is provided with the electroencephalogram electrode unit 1 described previously and simultaneous measuring equipment 30.

As shown in FIG. 15, the simultaneous electroencephalogram and f-MRI measuring equipment 30 using the electroencephalogram electrode unit 1 for small animals includes an electroencephalogram measuring equipment 10 and an f-MRI equipment 32. On the head of the small animal 12, the electroencephalogram electrode unit 1 is mounted.

The f-MRI equipment 32 is provided with a function of detecting the increase in blood flow at a brain area receiving stimuli in the case where the brain receives stimuli, in addition to the function of normal MRI device. The f-MRI equipment 32 includes: a magnetic field scanning unit 32a for applying magnetic field to a small animal 12, namely the target of observation; a control unit 32b for controlling the magnetic field scanning unit 32a and fetching NMR signals; and a personal computer 32c for receiving NMR signals from the control unit 32b and creating image data. T1, which is displayed as an image in the f-MRI equipment 32, represents longitudinal relaxation time in nuclear magnetic resonance. T1 is a value of matter dependent on the environment. Similarly, T2, which is displayed as an image in the MRI as well as T1, is traverse relaxation time in nuclear magnetic resonance and is a value unique to matter.

In the f-MRI equipment 32, if the blood flow of the small animal 12 increases by receiving stimuli in its brain, the concentration of reduced hemoglobin, which is a paramagnetic material, decreases along with magnetic susceptibility, causing T2 to increase.

Consequently, when the blood flow of the small animal 12 increases, resulting in increase in T2, the increase is detected as f-MRI signal increasing in the area where stimuli are applied on T2 highlighted image, namely stimulus activation area. This f-MRI signal was found by Dr. Ogawa et al. and is called the blood-oxygen-level-dependent (BOLD) effect (See Non-patent Reference 3). These f-MRI signals are normally measured using T2-star-highlighted image (T2*), the value obtained by taking into account the non-uniformity of magnetic field in addition to T2, which is conventional MRI signal.

Electroencephalogram is input from the electroencephalogram electrode unit 1 for the small animal 12 into a battery-type amplifier 14, and the output signal 15 from this amplifier 14 is input into an A/D converter 18 via optical fiber 36, for example. The output from the A/D converter 18 is processed with a personal computer 16, etc. for EEG signals, and the electroencephalogram signals are made into data.

Here, as described in the case of the variation of the first embodiment, the ECG measurement may be performed to remove the ballisto-cardiogram artifact of the small animal 12 in electroencephalogram measurement. As shown in FIG. 6, it is only necessary to be provided with an amplifier 22 for amplifying signals from the electrode for electrocardiogram measurement 19 and an interface circuit 18a for the ECG measurement. In the case of FIG. 15, EEG and ECG signals are input into the amplifier 14a having multi-channel inputs, and then connected to a personal computer 16 for signal processing via the A/D converter 18. Furthermore, the simultaneous electroencephalogram and f-MRI measuring equipment 30 may include a ventilator 37 for artificial ventilation of the small animal 12 and end-tidal $CO_2$ concentration monitoring equipment 38.

According to the simultaneous electroencephalogram and the f-MRI measuring equipment 30 using the electroencephalogram electrode unit 1 for small animals as shown in FIG. 15, 31-channel electroencephalogram measurement, for example, can be performed by the electroencephalogram electrode unit 1 for small animals.

Accordingly, the neural activity in 1 voxel level obtained by electroencephalogram measurement, 200 μm×200 μm for example, can be measured in a short time. Furthermore, the BOLD effect can also be measured based on the hemodynamic response function obtained by the f-MRI measurement of the small animal 12, to which stimuli are given. The EEG measurement system is capable of performing measurement outside the MRI device 30. The stimuli to the small animal 12 are applied from a stimulator 35 to the small animal 12.

(Example of Simultaneous Measurement of Electroencephalogram and f-MRI)

An example of simultaneous measurement of the electroencephalogram and the f-MRI measurement will be described.

As the f-MRI measuring equipment 32, commercially available equipment having a superconductive coil of a diameter of 38 mm (70/16 PharmaScan, Bruker Biospin, Germany) was used. The gradient in the magnetic field was 300 mT/m at the maximum. The f-MRI image was created by the echo planer method (EPI). The Paravision 5.0 was used as the software for measuring the f-MRI.

Before performing simultaneous electroencephalogram and f-MRI measurements of the small animal, the effect of electroencephalogram electrode unit 1a for small animals on the f-MRI measurement was examined.

To obtain a reference image, a dummy material for biometric measurement, so-called phantom, was prepared by filling a cylindrical polyethylene container having a diameter of 2 cm and length of 6 cm with a solution containing $NiCl_2$, etc. This phantom was inserted into the magnetic field scanning unit 32a, namely a gantry, of the f-MRI equipment 32. The f-MRI measurement was performed with the electroencephalogram electrode unit 1a for small animals mounted or not mounted on the phantom. The EPI image, T2 image, T2 mapping, T2* mapping, etc. were obtained as the reference images. It was found from these pieces of data that there is no difference in f-MRI measurement results between the case where the electroencephalogram electrode unit 1a for small animals was mounted to the phantom and the case where it was not mounted to the phantom.

As the small animal 12, a male Wistar rat 12a was used. As stimuli applied to the right forepaw of the Wistar rat 12a, pulse current generated from the stimulator 35 was used. Specifically, 3-mA pulse current was applied to the right forepaw of the Wistar rat 12a for 30 seconds, and then the stimulus was turned off for 40 seconds, which was regarded as one cycle, and over 10 cycles were repeated.

Figure 16:
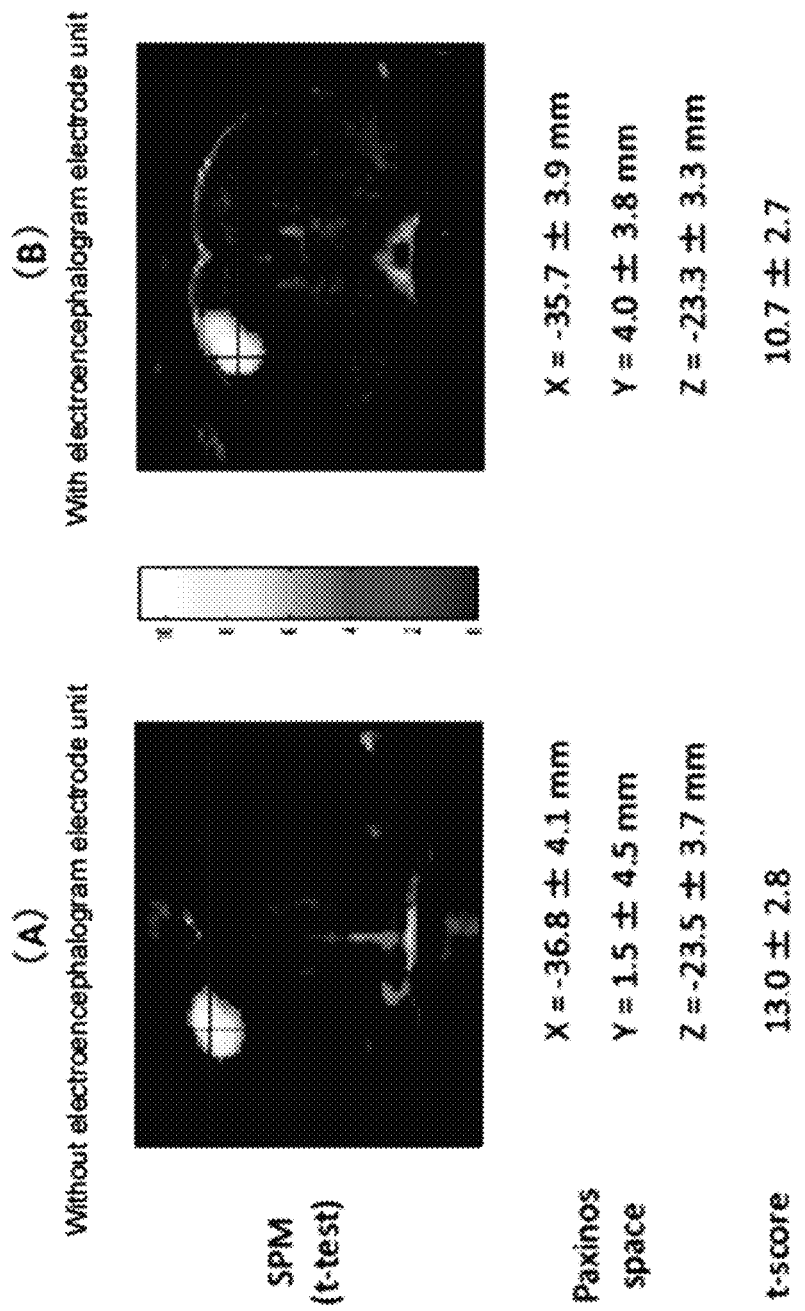
FIG. 16 provides f-MRI images obtained when stimuli by current pulse were applied to the right forepaw of a Wistar rat, wherein (A) shows the f-MRI image when the electroencephalogram electrode unit for small animals was not used and (B) shows the f-MRI image when the electroencephalogram unit for small animals was used.

FIG. 16 shows the f-MRI images obtained when stimuli by current pulse were applied to the right forepaw of the Wistar rat 12a, wherein (A) is the f-MRI image obtained when the electroencephalogram electrode unit for small animals was not mounted, and (B) is the f-MRI image obtained when the electroencephalogram electrode unit 1a for small animals was mounted. FIG. 16 also presents t-score of BOLD signals analyzed using software for f-MRI analysis (SPM software, Wellcome Department of Imaging Neuroscience, UK).

FIG. 16 (A) is a chart showing the change in BOLD signals observed with the f-MRI equipment when stimulus by current pulse was applied 10 times repeatedly to the right forepaw of the Wistar rat 12a. It is apparent that in response to the current stimulus time applied to the right forepaw of the Wistar rat 12a, the BOLD signal increased.

As shown in FIG. 16 (A), the position where the BOLD signal increased when the electroencephalogram electrode unit 1a for small animals was not mounted is represented as follows on the brain map of the rat by Paxinos, etc. in XYZ notation.

$X=-36.8\pm4.1$ mm $Y=1.5\pm4.5$ mm $Z=-23.5$ mm$\pm3.7$ mm

Meanwhile, as shown in FIG. 16 (B), the position where the BOLD signal increased when the electroencephalogram electrode unit 1a for small animals was mounted is represented as follows on the brain map of the rat by Paxinos, etc. in XYZ notation.

$X=-35.7\pm3.9$ mm $Y=4.0\pm3.8$ mm $Z=-23.3$ mm$\pm3.3$ mm

In addition, as shown in FIG. 16 (A), t-score ($p<0.001$, where P is significance probability) of BOLD signals by SPM software when the electroencephalogram electrode unit 1a was not mounted was $13.0\pm2.8$.

Meanwhile, as shown in FIG. 16 (B), t-score of BOLD signals by SPM software when the electroencephalogram electrode unit 1a was mounted was $10.7\pm2.7$.

From the results shown above, it was found that when a stimulus by current pulse was applied to the right forepaw of the Wistar rat 12a, the brain received the stimulus at approximately the same X, Y, Z positions on the brain map both in the case where the electroencephalogram electrode unit 1a for small animals was mounted and the case where it was not mounted. Furthermore, SPM software analysis revealed that the BOLD signals give approximately the same signal intensity.

Figure 17:
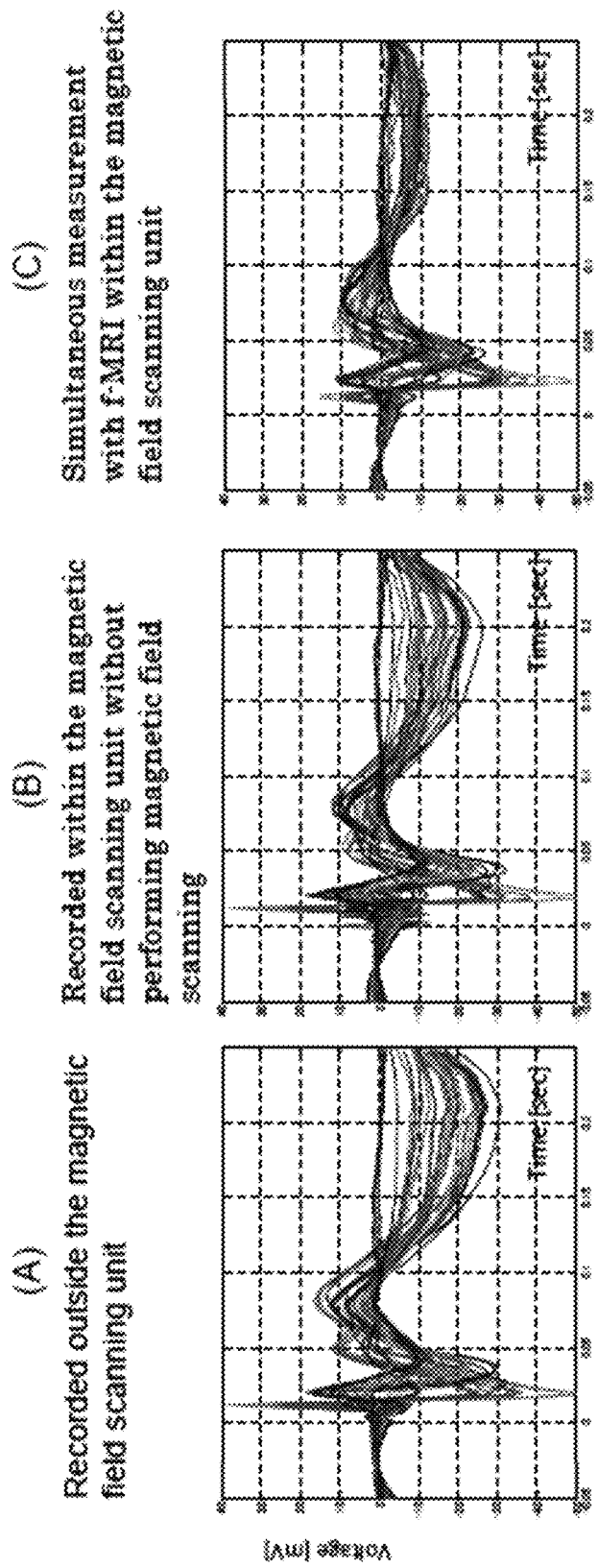
FIG. 17 provides f-MRI images of averaged EEG signals obtained when stimuli by 900-times current pulses were applied to the right forepaw of a Wistar rat, wherein (A) shows signals recorded outside a magnetic scanning unit, (B) shows signals recorded within a magnetic scanning unit by not performing magnetic scanning, and (C) shows signals recorded within the magnetic scanning unit by performing simultaneous measurement with f-MRI.

FIG. 17 provides charts showing averaged EEG signals when stimulus by current pulse was applied 900 times to the right forepaw of the Wistar rat 12a, wherein (A) is the case where recording was made outside the magnetic field scanning unit 32a, (B) is the case where recording was made within the magnetic field scanning unit 32a without performing magnetic field scanning, and (C) is the case where f-MRI measurement was performed simultaneously within the magnetic field scanning unit 32a. The horizontal axis in FIG. 17 represents time (second), and the vertical axis in FIG. 17 represents electroencephalogram signal voltage (mV). Each chart shows the pieces of data from 30 electrode sections 6 superimposed.

The EEG signal as shown in FIG. 17 (C) is a result obtained by removing scanning artifact of EPI image related to obtainment of BOLD signals by performing arithmetic operation using a personal computer 16, with the periodic signal used as the reference signal.

It was found from the results described above that when stimulus by current pulse was applied to the forepaw of the Wistar rat 12a 900 times, approximately the same averaged EEG signals were given in all of the cases. The recording was made outside the magnetic field scanning unit 32a (FIG. 17 (A)), the recording was made within the magnetic field scanning unit 32a without performing magnetic field scanning (FIG. 17 (B)), and the measurement was made simultaneously by f-MRI within the magnetic field scanning unit 32a (FIG. 17 (C)).

As described above, it was found from the experiments of the BOLD signal as shown in FIG. 16 and the EEG signal as shown in FIG. 17 that the multi-channel electroencephalogram measurement and the f-MRI measurement can be performed simultaneously and successfully by using the electroencephalogram electrode unit 1a for small animals of the present invention. Such measurement has never been achieved to the best of the present inventor's knowledge.

The present invention makes it possible to perform the simultaneous electroencephalogram and f-MRI measurements of small animals 12. By using electroencephalogram measurement, neural activities can be measured with high temporal resolution. By using f-MRI, neural activities can be measured simultaneously with high spatial resolution. Consequently, the simultaneous electroencephalogram and f-MRI measurements can provide ideal non-invasive brain activity measurement system that compensates advantages and disadvantages of each. Furthermore, as described later, the electrode can also be replaced with a probe for near infrared spectroscopy (called as NIRS).

(Fourth Embodiment)

The electroencephalogram electrode unit 50 for small animals in a fourth embodiment of the present invention will then be described.

Figure 18:
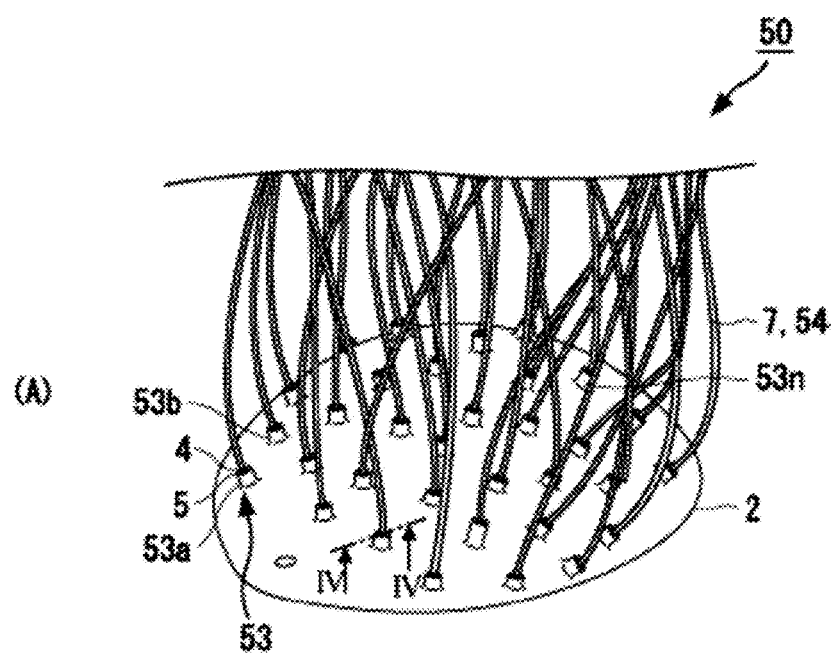
FIG. 18 shows the structure of the electroencephalogram electrode unit for small animals in a fourth embodiment of the present invention, wherein (A) is an oblique perspective view and (B) is a cross-sectional view along the line IV-IV in (A).
Figure 18:
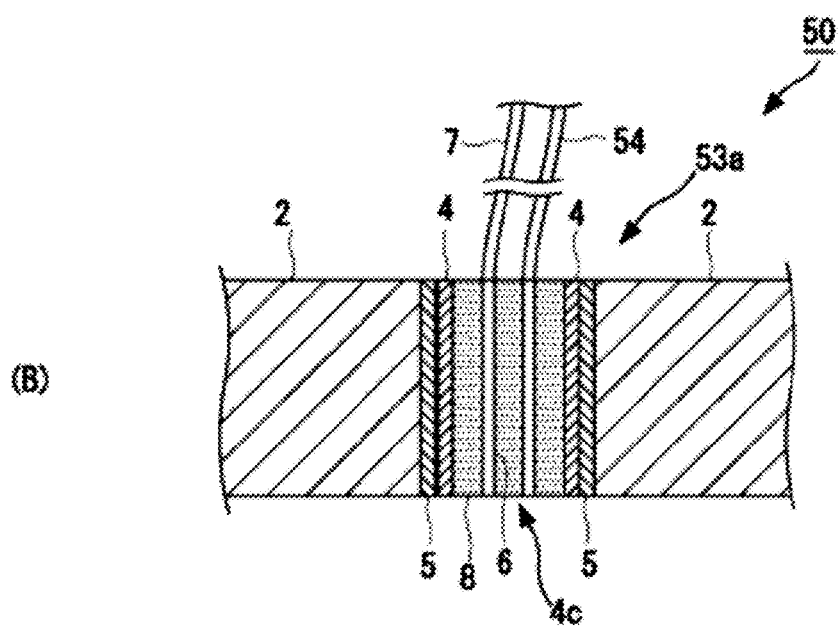

FIG. 18 shows the structure of electroencephalogram electrode unit 50 for small animals in the fourth embodiment of the present invention, wherein (A) is an oblique perspective view and (B) is a cross-sectional view along the line III-III in (A).

As shown FIG. 18 (A), the electroencephalogram electrode unit 50 for small animals of the present invention includes: a base 2 to be placed covering the scalp or brain surface; and a plurality of electrodes 53 (53a to 53n) inserted into the base 2.

As shown in FIG. 18 (B), one electrode 53a includes: an inner first tube 4; an outer second tube 5; an electrode section 6 and optical fibers 54 inserted into the inner first tube 4; an extraction conducting wire 7 of this electrode section 6; and paste 8 that is filled within the inner first tube 4.

Unlike the electroencephalogram electrode units 1, 1a for small animals as shown in FIGS. 1 and 2, the electroencephalogram electrode unit 50 for small animals as shown in FIG. 18 is further provided with optical fibers 54 to be inserted into the inner first tube 4. One electrode 53 is provided with one electrode section 6, and the number of electrodes 53 to be provided on the entire base 2 can be determined arbitrarily. The number of electrodes 53 can be approximately 30 to 40, for example. The number of optical fibers 54 can be the same as or different from that of electrodes 53. The number of optical fibers 54 can be determined in accordance with the near infrared spectroscopy to be described later. One end of the optical fibers 54 of the electroencephalogram electrode unit 50 for small animals contacts the brain or scalp of the small animal 12 as in the case of the electrode section 6, irradiating near infrared light deep into inside the brain. The structure other than the optical fibers 54 has already been described and so description will be omitted. FIG. 18 (B) shows the structure wherein the electrode section 6 is inserted deep into the inner tube 4 along with the optical fibers 54 so that it contacts the scalp, but needless to say, shorter length may be selected for the electrode section 6 in this embodiment so that the bottom end comes apart from the bottom opening 4*c* of the tube 4 as in the case of the electrode section 6 shown in FIGS. 1, 2 and 4.

The optical fibers 54 of the electroencephalogram electrode unit 50 for small animals are those for performing near infrared spectroscopy, and has low loss at wavelength, 800 nm for example, allowing absorption spectroscopy of hemoglobin and oxygen in the brain to be performed. As such an optical fiber 54, quartz glass for optical communication and resin optical fibers 54 can be used.

The other end of the optical fiber 54 is connected to a so-called near infrared spectrometer, the infrared ray for spectroscopy is irradiated to small animals, and then the reflected light is detected.

According to the electroencephalogram electrode unit 50 for small animals of the present invention, the near infrared ray spectroscopy (NIRS) measurement can be performed simultaneously with electroencephalogram measurement. Furthermore, electrocardiogram measurement can also be performed at the same time.

The present invention is not limited to the embodiments described above, but various variations are allowed within the scope of the present invention specified in the claim, and it goes without saying that they are included in the scope of the present invention.

INDUSTRIAL APPLICABILITY

By performing simultaneous the electroencephalogram and the f-MRI measurement using the electroencephalogram electrode units 1, 1*a*, 1*b*, and 50 for small animals of the present invention, pharmacologic screening such as using a knockout mouse having specific invalidated gene and enzyme-inhibiting agent can be performed for small animals, which cannot be performed using humans. Furthermore, a major advantage is that mutual data comparison with conventional brain immunostaining, fluorescent staining, and electrophysiological method is allowed.

The simultaneous electroencephalogram and the f-MRI measurement of the present invention can be combined with various pharmacological and genetic methods, and thus can be an innovative drug evaluation system not only in basic research field of brain neuroscience but also in the pharmaceutical industry.

DESCRIPTION OF CODES

1, 1*a*, 1*b*, 50: Electroencephalogram electrode unit for small animals
2: Base
2*a*: Through hole
3: Electrode section
4: First tube
4*a*: Cap
4*b*: Upper opening of the first tube
4*c*: Lower opening of the first tube
5: Second tube
6: Electrode
7: Extraction conducting wire
8: Paste
9: Opening
10: Electroencephalogram measuring equipment using the electroencephalogram electrode unit for small animals
10*a*: Electroencephalogram and electrocardiogram measuring equipment using the electroencephalogram electrode unit for small animals
12: Small animal
12*a*: Wistar rat
14, 14*a*: Amplifier
15: Output signal from the amplifier
16: Computer
18, 18*a*: Interface circuit
19: Electrode for electrocardiogram measurement
22: Amplifier for ECG
30: Simultaneous electrocardiogram and functional MRI measuring equipment using the electrocardiogram electrode unit for small animals
32: f-MRI equipment
32*a*: Magnetic field scanning unit
32*b*: Control unit
32*c*: Computer
35: Stimulator
36: Optical fiber
37: Ventilator
42: Electrode for intracranial measurement
42*a*: Electrode section
42*b*: Terminal area
42*c*: Electrode
38: Terminal expiratory $CO_2$ concentration monitoring equipment
53: Plurality of electrodes
54: Optical fiber
100: Electroencephalogram measurement system
200: Simultaneous electroencephalogram and f-MRI measurement system

What is claimed is:

1. An electroencephalogram electrode unit for small animals, comprising:
    a base that covers a scalp or brain surface of a small animal and has a plurality of through holes; and
    a plurality of electrodes,
    wherein each of the plurality of electrodes is inserted into one of the plurality of through holes;
    wherein each of the plurality of electrodes is equipped with an insulating inner first tube, an insulating outer second tube housing the first tube, an electrode section disposed within the first tube, an extraction conducting wire that is connected to the electrode section and for taking electroencephalogram signals to outside, and a paste filled within the first tube;
    wherein the first tube and the second tube are installed in the through hole in a manner of standing upright from the scalp or brain surface; and
    wherein the electrode section is formed in a form of a wire and is disposed, in a manner of standing upright from the scalp or brain surface, within the paste filled within the first tube.

2. The electroencephalogram electrode unit for small animals as set forth in claim 1, wherein the first tube is inserted in a state movable in the axial direction of the second tube.

3. The electroencephalogram electrode unit for small animals as set forth in claim 1 or 2, wherein a bottom end and a side surface of the electrode section contact the paste.

4. The electroencephalogram electrode unit for small animals as set forth in claim 1 or 2, wherein the paste is a mixture of a paste for electroencephalogram and a physiological saline solution.

5. The electroencephalogram electrode unit for small animals as set forth in claim 1 or 2, wherein the base is further equipped with an opening, into which an electrode for intracranial measurement can be inserted.

6. The electroencephalogram electrode unit for small animals as set forth in claim 1 or 2, wherein the first tube is further equipped with an optical fiber.

7. The electroencephalogram electrode unit for small animals as set forth in claim 1 or 2, wherein the material of the electrode is a metal selected from the group consisting of platinum, gold, silver, stainless steel, iridium, and tin.

8. The electroencephalogram electrode unit for small animals as set forth in claim 1 or 2, wherein the conductivity of the paste falls within a range from 0.01 S/m to 10 S/m.

\* \* \* \* \*